United States Patent [19]

Duerr et al.

[11] Patent Number: 5,549,475
[45] Date of Patent: Aug. 27, 1996

[54] ENOSSAL SINGLE-TOOTH IMPLANT

[75] Inventors: Walter Duerr, Remchingen; Axel Kirsch, Stuttgart, both of Germany

[73] Assignees: Eberle Medizintechnische Elemente GmbH, Wurmberg; IMZ Fertigungs-und Vertriebsgesellschaft fuer dentale Technologie mbH, Filderstadt, both of Germany

[21] Appl. No.: 352,507

[22] Filed: Dec. 9, 1994

[30] Foreign Application Priority Data

Dec. 9, 1993 [DE] Germany .......................... 43 42 058.3

[51] Int. Cl.⁶ ...................................................... A61C 8/00
[52] U.S. Cl. ............................................................. 433/173
[58] Field of Search ...................................... 433/172, 173, 433/174, 175, 176

[56] References Cited

U.S. PATENT DOCUMENTS

| | | | |
|---|---|---|---|
| 5,026,285 | 6/1991 | Dürr et al. | 433/173 |
| 5,049,073 | 9/1991 | Lauks | 433/173 |
| 5,106,300 | 4/1992 | Voitik | 433/173 |
| 5,125,840 | 6/1992 | Dürr et al. | 433/173 |
| 5,145,371 | 9/1992 | Jürnéus | 433/173 |
| 5,152,687 | 10/1992 | Amino | 433/173 |
| 5,213,500 | 5/1993 | Salazar et al. | 433/173 X |

FOREIGN PATENT DOCUMENTS

| | | |
|---|---|---|
| 3917690 | 6/1991 | Germany . |
| 4028856 | 6/1992 | Germany . |
| 4028855 | 10/1992 | Germany . |

*Primary Examiner*—Nicholas D. Lucchesi
*Attorney, Agent, or Firm*—Hill, Steadman & Simpson

[57] ABSTRACT

An enossal single-tooth implant for tightly-fitting dentures, characterized by a substantially cylindrical basic body inserted in a bore made in the jawbone and having a blind bore opening to an outer end, a spacing sleeve engageable on the outer end of the basic body, an implant post insertable in the blind bore of the basic body and connectible in a rotation-prevented manner to the basic body, a joining device for fixing the spacing sleeve to the basic body and a fixing head for the denture joined to the implant post. The implant includes that the fixing head and the joining device are constructed as a one-piece bell-shaped hood having a tapering skirt, which concentrically surrounds the implant post and whose skirt engages over the joint area between an outer circumference of the basic body and the spacing sleeve, with the tapering skirt area being constructed in such a way that it gently extends over a cylindrical circumferential wall of the basic body.

14 Claims, 2 Drawing Sheets

5,549,475

ENOSSAL SINGLE-TOOTH IMPLANT

BACKGROUND OF THE INVENTION

The present invention is directed to an enossal implant, which is also known as an endosteal or endosseous implant. The enossal single-tooth implant of the present invention is for a tight-fitting denture and substantially includes a cylindrical basic body insertable in a bore made in the jawbone, which body has a blind bore opening at a coronal end with a coronal front edge, a spacing sleeve engageable on the coronal front edge of the basic body, means for holding the spacing sleeve on the basic body and in a rotation-preventing manner, an implant post with a fixing head for the denture.

U.S. Pat. No. 5,125,840, whose disclosure is incorporated herein by reference thereto and which claims priority from German Application 40 28 855, discloses an enossal single-tooth implant. The implant of this patent has an outer circumference of a spacing sleeve which forms an outer face or surface of an implant in a subgingival contact with the surrounding tissue and between the basic body and a spacing sleeve there is necessarily a joint area. To hold the spacing sleeve on the basic body, a fixing head is provided. The spacing sleeve is connected to the basic body in a rotation-prevented manner and has means for forming a rotation-preventing connection to the denture and, therefore, forms necessarily additional joint areas on the outer circumference of the implant. The basic body, spacing sleeve and fixing head are prefabricated parts which only can be adapted to a limited extent to the anatomical features of a specific patient. The basic body, the spacing sleeve, the implant post and the fixing head, preferably, are made from a body tissue-friendly titanium alloy.

The known single-tooth implant has proven fundamentally satisfactory, but it has proven desirable to be able to further improve the adaptation of the implant to specific or special characteristics of the body. It is also desirable to substantially reduce the subgingival joint areas on the outer circumference or surface of the implant.

SUMMARY OF THE INVENTION

It is an object of the present invention to provide an improved single-tooth implant which has better adaptation to special anatomical features of the individual patient, and also avoids, to the greatest possible extent, joint areas on the outer circumference or surface of the implant.

Accordingly, it is an object of the present invention to provide an improvement in a single-tooth implant for a tightly-fitting denture, which implant includes a cylindrical basic body insertable in a bore made in the jawbone, said body having a blind bore opening to an open end with an outer front edge, a spacing sleeve engageable on the open end of the outer front edge of the basic body, an implant post insertable in the blind bore of the basic body and connectible in a rotation-prevented manner to the basic body, a joining device for fixing the spacing sleeve to the basic body and a fixing head for the denture joined to the implant post. The improvements are that the fixing head and the joining device are constructed as a one-piece tapering bell-shaped ring hood concentrically surrounding the implant post and whose ring-shaped skirt extends over the joint area between the outer circumference of the basic body and the spacing sleeve and in that the tapering area thereof is constructed in such a way that it gently merges with a cylindrical circumferential wall of the basic body.

The basic body can have, close to its coronal or open end on its outer circumference, an all-around annular constriction for receiving a tapering front edge of the annular skirt of the ring hood.

The invention also proposes that the ring hood is constructed in one piece with the implant post.

According to another embodiment, the implant post and the ring hood are jointly cast.

According to the invention, it is also possible for the ring hood to be provided with the denture at its upper or outer end prior to joining to the basic body.

The invention optionally also proposes that the denture be manufactured, at least in part, in one piece with the ring hood.

A further embodiment of the invention is characterized in that the ring hood and denture are jointly cast.

The invention is particularly characterized in that the blind bore of the basic body is provided in a narrow or neck-like area with an internal thread and, in its open end, has a ring or annular recess with a smooth inner wall extending up to the outer or coronal front edge of the basic body, which annular recess has a larger diameter than the diameter of the area of the blind bore provided with the internal threads. The spacing sleeve is provided with a centering collar, whose external diameter corresponds to the internal diameter of the annular recess and has a shoulder for engaging on the outer front edge of the basic body. The tapering face of the centering collar and the annular shoulder of the basic body complementary thereto and bounding the annular recess with respect to the area of the blind bore of the basic body provided with internal threads are provided, in each case, with at least one complementary interlocking member for the rotation-prevented fixing of the spacing sleeve with respect to the basic body. The inner sleeve is provided with a cervical area or neck portion with external threads corresponding to the internal threads of the basic body and the inner sleeve has a smooth external diameter in the vicinity of the centering collar of the spacing sleeve corresponding to the inner diameter of the spacing sleeve. The inner sleeve is provided with an outwardly extending shoulder at its free end for engaging the free end of the spacing sleeve. When the internal sleeve is threaded into the basic body, it will press the spacing sleeve into interlocking, rotation-prevented engagement with the basic body and the implant post can be fixed in an open end internal bore of the internal sleeve.

According to the invention, the implant post can be cemented into the internal bore of the internal or inner sleeve.

The invention also proposes that the implant post can be screwed into the internal bore of the inner sleeve.

On the coronal end or outer end, the internal sleeve has a fastening device for a screw-in tool. The invention also proposes that the inner sleeve fastening device is formed by a polygonal construction of the free outer edge area of the internal sleeve.

According to a further embodiment, the spacing sleeve, close to its outer front edge on its outer wall, will have at least one indentation for receiving cement for rotation-prevented joining of the ring hood to the spacing sleeve. The single implant according to the invention can also be characterized in that close to its outer front edge, the spacing sleeve has an all-around concave construction or recess.

The invention is based on the surprising finding that it is possible to improve the single-tooth implant according to the prior art in a drastic manner with respect to its permanent integratability into the jaw. Instead of a sandwich construction herebefore considered necessary, in which the basic body is inserted in the jawbone successively and a number of individual components are engaged in a rotation-prevented manner on the body, as disclosed in U.S. Pat. No. 5,026,285, whose disclosure is incorporated herein by reference thereto and which claims priority from German Patent Application 39 17 690, the ring hood of the present invention is provided, which is preferably correctly anatomically cast with the implant post and adapted to the particular patient. This ring hood will engage and extend over the components of the implant not prosthetically adapted to the special anatomical features of the particular patient and the hood is closed to the outside so that the subgingival regions are optimally adapted on the outer wall of the implant to the body tissue and the individual jaw shape is ensured.

The complete implant is encapsulated so that its outer wall is formed solely by the basic body and the annular ring hood, as well as the denture, which is in the form of a crown and which is preferably also constructed in one piece with the annular hood. In a particular preferred embodiment, the crown, the implant post and the annular hood or ring hood are cast in accordance with an anatomically correct impression and then, after removing the normally used locking screw, the implant post is inserted into the blind bore of the basic body, which has already grown into the jawbone and the post is then cemented in at this point.

As a result of the construction according to the present invention, the healing process for the single implant can be significantly improved so that there are much longer use times compared to the known implants.

The demands to be made on the patient with respect to dental hygiene and keeping the denture and the exposed parts of the implant clean can be much more easily fulfilled than in the case of the known single-tooth implants.

Other advantages and features of the invention will be readily apparent from the following description of the preferred embodiments, the drawings and claims.

DESCRIPTION OF THE PREFERRED EMBODIMENTS

Figure 1:
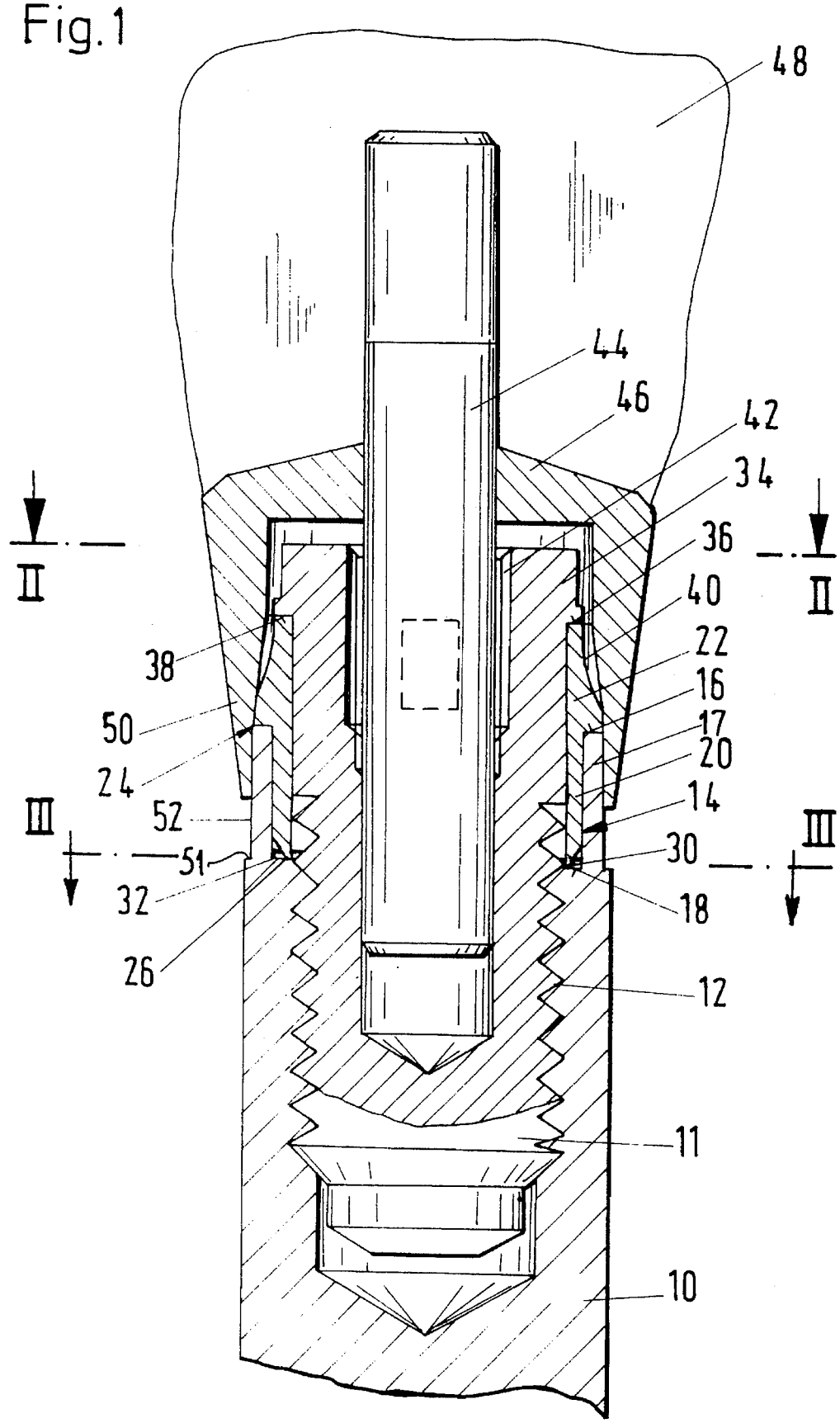
FIG. 1 is a cross sectional view along a median longitudinal axis of the single-tooth dental implant in accordance with the present invention while in the assembled state.
Figure 2:
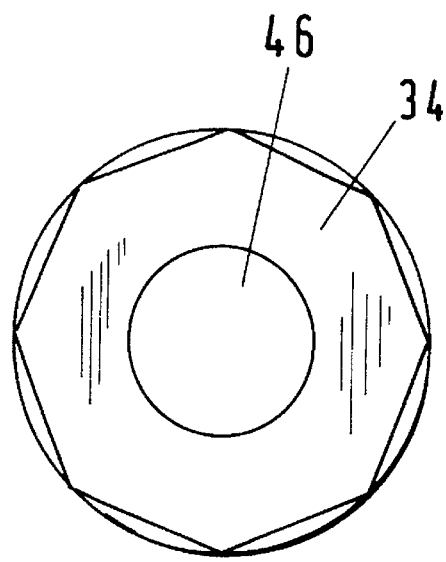
FIG. 2 is an end view of the inner sleeve of the single-tooth implant taken in the direction of arrows II—II of FIG. 1.

The principles of the present invention are particularly useful in a single-tooth implant illustrated in FIG. 1. As illustrated, a titanium alloy basic body 10, whose lower outer portions are substantially of the same structure as the basic body disclosed in U.S. Pat. No. 5,125,840, has a blind internal bore 11 which is open on an outer or coronal end, which is illustrated at the top of FIG. 1. The internal bore 11 has two different diameters, with the narrower or cervical diameter being provided with internal threads 12. Close to an outer or coronal end, the basic body 10 has a ring or annular recess 14, which is formed by an annular circumferential wall 17, extends up to the open end to form a circular front or outer edge 16 of the basic body 10. The internal diameter of the annular recess 14 is larger than the internal diameter of the blind bore 11 of the basic body area in the vicinity of the internal threads 12. At the connection of the threads 12 with the annular recess 14, a radial shoulder 18 is provided. The circumferential wall 17 has an outer radial shoulder 51 so that an outer surface 52 is recessed or forms an annular constriction.

Figure 3:
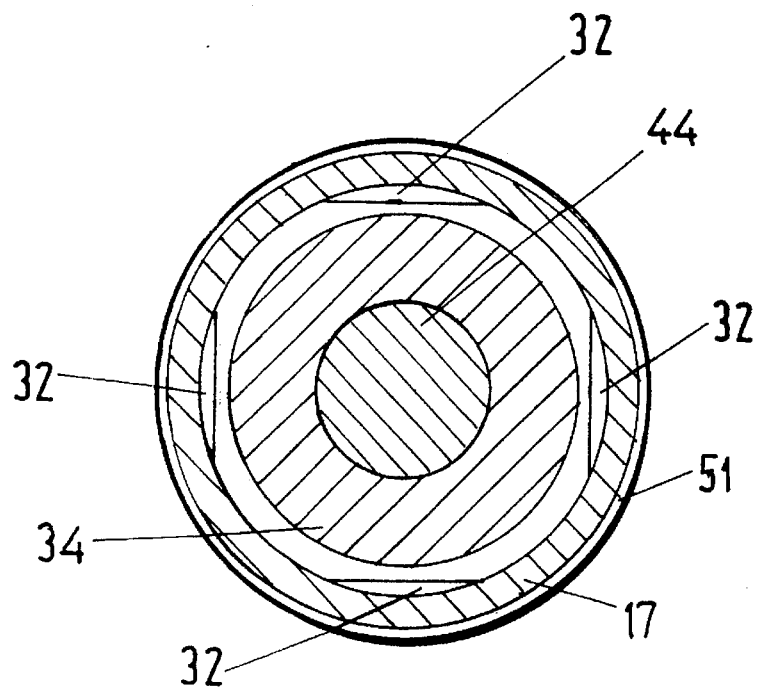
FIG. 3 is a cross sectional view taken along the lines III—III of FIG. 1 showing the relationship of the recesses and tongue for forming complementary interlocking elements between the basic body and the spacing sleeve.

The annular recess 14 of the basic body 10 receives a centering collar 20 of a spacing sleeve 22, which is also made from titanium alloy. The spacing sleeve 22 is provided with a radially extending shoulder 24 which engages on the front or outer edge 16 of the basic body 10. The centering collar 20 of the spacing sleeve 22 has an end face 26, which faces the annular shoulder 18 of the basic body. This surface of the sleeve and the shoulder 18 are provided with complementary interlocking elements in the form of tongues and recesses which correspond to the spacing sleeve interlocking elements between the spacing sleeve upper part and the basic body according to U.S. Pat. No. 5,125,840. If desired, these tongues and recesses can have the same construction as those disclosed in this U.S. Patent. As illustrated in FIG. 3, the shoulder 18 has upstanding tongues 32 which have a shape of part of a circle and are received in corresponding recesses in the end face 26 of the sleeve 22.

An inner sleeve 34 is threaded into the internal threads 12 of the basic body 10 and the sleeve 34 is also made from a titanium alloy. The sleeve 34 has a radial shoulder 36 close to its outer end, which shoulder 36 engages an outer front edge 38 of the spacing sleeve 22. In this way, the inner sleeve 34 presses the spacing sleeve 22 against the basic body 10 in such a way that through the interlocking engagement of the interlocking tongues and interlocking recesses, the spacing sleeve 22 is joined in a rotation-prevented manner to the basic body 10. In the outer region, the spacing sleeve 22 is provided with a concave annular indentation or recess 40.

The inner sleeve 34 has an inner bore 42 which is opened at a coronal or outer end and receives a cylindrical implant post 44, which is cast in one piece with a bell-shaped ring or annular hood 46 from a metal, such as used in dental prosthetics or crown structures and the like. The denture in the form of a crown 48 is firmly connected to the annular hood or ring hood 46. The ring hood 46 has a tapering annular skirt 50 which will engage over the outer end of the basic body 10 and the ring skirt 50 passes gently onto an annular constriction or outer surface 52 of an annular circumferential wall 17 of the basic body 10.

The ring hood 46, optionally with the crown 48, is constructed in one piece with the implant post 44 and the hood 46 and post 44 are cast in one piece in accordance with the individual requirements of the particular patient. Accompanied by the sliding of the ring hood 46 over the coronal edge of the basic body 10, the implant post 44 is inserted in the inner bore 42 of the inner sleeve 34 and bonded thereto. The indentation 40 on the outer circumference of the spacing sleeve 22 is filled with cement, so that the ring hood 46 can be joined in a rotation-prevented manner to the spacing sleeve 22, which is joined in a rotation-prevented manner to the basic body 10 by the cooperation of the interlocking elements 30 and 32. Thus, due to the fact that unlike in the case of the hitherto known sandwich structures, there is only a single joining area between the ring hood 46 and the outer circumference of the basic body 10. In conjunction with this anatomical adaptation of the shape of the ring hood 46 to the special features of the particular patient, considerably improved adaptation occurs in the subgingival region compared with the known constructions.

The drawings also show that close to the outer end on an outer circumference, the inner sleeve 34 has a polygonal construction. Thus, by means of a corresponding spanner, it is possible to ensure a completely satisfactory threading of the inner sleeve 34 into the basic body 10.

Although various minor modifications may be suggested by those versed in the art, it should be understood that we wish to embody within the scope of the patent granted hereon all such modifications as reasonably and properly come within the scope of our contribution to the art.

We claim:

1. In a single-tooth implant for a tightly-fitting denture, said implant having a cylindrical basic body insertable in a bore made in a jawbone, said body having a blind bore open to an open end to form a coronal front edge, a spacing sleeve engageable on the coronal front edge, an implant post inserted in the blind bore of the basic body and connectible in a rotation-preventing manner to the basic body, a joining device for fixing the spacing sleeve on the basic body and a fixing head for the denture joined to the implant post, the improvements comprising the fixing head and the joining device being constructed as a one-piece member having a bell-shaped ring hood with a tapering skirt concentrically surrounding the implant post, said tapering skirt extending over the joint area between the outer circumference of the basic body and the spacing sleeve, said tapering skirt extending over a cylindrical circumferential wall of the basic body.

2. In a single-tooth implant according to claim 1, wherein adjacent the coronal front edge, an outer circumference of the basic body has an annular constriction for receiving the tapering skirt of the ring hood.

3. In a single-tooth implant according to claim 1, wherein the ring hood is constructed in one piece with the implant post.

4. In a single-tooth implant according to claim 1, wherein the implant post and the ring hood are jointly cast.

5. In a single-tooth implant according to claim 1, wherein an upper surface of the ring hood is provided with a denture prior to joining of the ring hood to the basic body.

6. In a single-tooth implant according to claim 5, wherein the ring hood and at least a part of the denture are formed as a single piece.

7. In a single-tooth implant according to claim 6, wherein the ring hood and denture are a jointly cast member.

8. In a single-tooth implant according to claim 1, wherein the blind bore of the basic body is provided with a narrow diameter portion having internal threads and, adjacent the coronal edge of the basic body, the blind bore has an annular recess with a smooth inner wall of a larger diameter to form an internal shoulder with the narrow diameter portion, the spacing sleeve being provided with a centering collar, whose external diameter corresponds to the internal diameter of the annular recess and has a shoulder for engaging the coronal front edge of the basic body, said centering collar having an end face for engaging the radial shoulder of the basic body, said end face and shoulder being provided with at least one complementary interlocking member for rotation-prevented fixing of the spacing sleeve with respect to the basic body, an inner sleeve being provided having a threaded portion for engagement in the threaded bore of the basic body, and a smooth external diameter in the vicinity of the centering collar of the spacing sleeve corresponding to the internal diameter of the spacing sleeve, said inner sleeve terminating in a radial shoulder for engaging an exposed end of the spacing sleeve to press the spacing sleeve into interlocking rotation-preventing engagement with the basic body, said inner sleeve having an internal bore for receiving the implant post.

9. In a single-tooth implant according to claim 8, wherein the implant post is cemented into the internal bore of the inner sleeve.

10. In a single-tooth implant according to claim 8, wherein the internal bore of the inner sleeve is provided with threads and the implant post is threaded therein.

11. In a single-tooth implant according to claim 8, wherein an outer end of the inner sleeve has flat surfaces for engagement with a tool for threading the inner sleeve into the threaded bore.

12. In a single-tooth implant according to claim 11, wherein the flat surfaces are formed by a polygon construction of the outer end of the inner sleeve.

13. In a single-tooth implant according to claim 8, wherein the spacing sleeve adjacent an outer end has at least one indentation for receiving cement for the rotation-prevented joining of the ring hood on the spacing sleeve.

14. In a single-tooth implant according to claim 8, wherein the spacing sleeve adjacent an outer end is provided with an outer annular recess for receiving cement for securing the ring hood thereon.

* * * * *